United States Patent
Omatsu et al.

(10) Patent No.: US 6,336,964 B1
(45) Date of Patent: *Jan. 8, 2002

(54) OZONE INDICATOR AND OZONE SENSOR INK

(75) Inventors: Takeshi Omatsu, Kyoto-fu; Hiroshi Inoue, Osaka-fu, both of (JP)

(73) Assignee: Sakura Color Products Corporation, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/612,720

(22) Filed: Jul. 10, 2000

Related U.S. Application Data

(63) Continuation of application No. 09/083,953, filed on May 22, 1998, now Pat. No. 6,117,685.

(30) Foreign Application Priority Data

| May 22, 1997 | (JP) | ................................................ 9-132652 |
| Sep. 1, 1997 | (JP) | ................................................ 9-236347 |
| Nov. 11, 1997 | (JP) | ................................................ 9-308774 |

(51) Int. Cl.[7] .......................... G01N 31/22; C09D 11/02
(52) U.S. Cl. .................. 106/31.44; 106/31.32; 106/31.59
(58) Field of Search .................. 106/31.32, 31.44, 106/31.59

(56) References Cited

U.S. PATENT DOCUMENTS

| 3,397,966 A | 8/1968 | Plantz .......................... 436/135 |
| 3,568,627 A | 3/1971 | Selinger et al. ............. 116/207 |
| 3,704,096 A | 11/1972 | Verses et al. .................. 436/1 |
| 3,914,174 A | 10/1975 | Fuchs .......................... 210/658 |
| 4,772,560 A | 9/1988 | Attar ............................ 436/135 |
| 4,859,607 A | 8/1989 | Lambert et al. ............ 436/135 |
| 5,178,831 A | 1/1993 | Sakota et al. .................. 422/56 |
| 5,281,662 A | 1/1994 | Ito et al. ..................... 525/54.1 |
| 5,480,611 A | 1/1996 | Mills et al. ................... 422/55 |
| 5,480,702 A | 1/1996 | Matsumoto et al. ........ 428/209 |
| 5,667,572 A | 9/1997 | Taniguchi et al. ....... 106/31.36 |
| 5,722,322 A | 3/1998 | Watanabe ................ 106/31.26 |
| 6,117,685 A | * 9/2000 | Omatsu et al. ............. 436/135 |

FOREIGN PATENT DOCUMENTS

| DE | 196 16 226 | 5/1996 |
| JP | 62-291564 | 12/1987 |
| JP | 05-165254 | 7/1993 |
| JP | 06-082410 | 3/1994 |
| JP | 09-220277 | 8/1997 |

* cited by examiner

Primary Examiner—C. Melissa Koslow
(74) Attorney, Agent, or Firm—Knobbe, Martens, Olson & Bear, LLP

(57) ABSTRACT

The invention provides a method of detecting ozone expediently and with high sensitivity. The invention, therefore, is directed to an ozone indicator comprising (1) at least one color-change layer comprised of an ozone sensor ink and (2) at least one non-color change layer both formed on a substrate, said color-change and non-color-change layers being formed in such a manner that at least a part or the whole of at least one color-change layer can be exposed to an ozone-containing atmosphere when the ozone indicator is put to use. The invention is further directed to an ozone sensor ink containing an anthraquinone dye having at least one amino group selected from primary and secondary amino groups.

12 Claims, 3 Drawing Sheets

FIG. 6
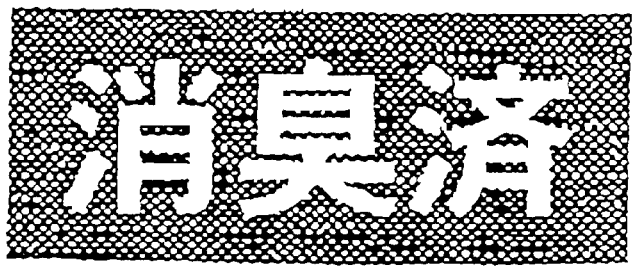
FIG. 7
IP. SAKURA COLOR PRODUCTS CORP. SAKURA COLI
SAKURA COLOR PRODUCTS CORP. SAKURA COLOR
IP. SAKURA COLOR PRODUCTS CORP. SAKURA COLI
SAKURA COLOR PRODUCTS CORP. SAKURA COLOR
IP. SAKURA COLOR PRODUCTS CORP. SAKURA COLI
SAKURA COLOR PRODUCTS CORP. SAKURA COLOR.
IP. SAKURA COLOR PRODUCTS CORP. SAKURA COLI
FIG. 8
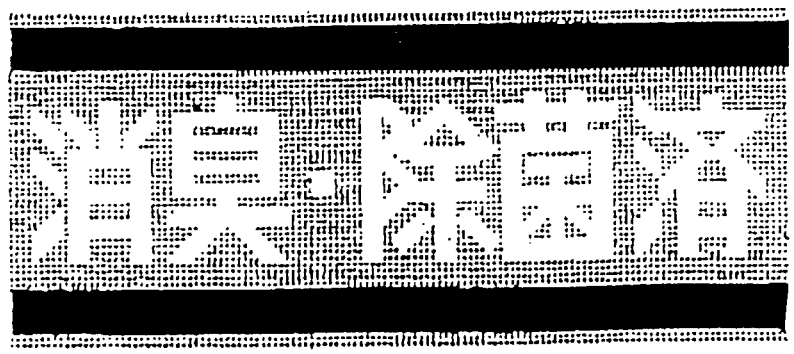

OZONE INDICATOR AND OZONE SENSOR INK

This is a continuation of application Ser. No. 09/083,953 filed May 22, 1998, now U.S. Pat. No. 6,117,685.

FIELD OF THE INVENTION

The present invention relates to an ozone indicator and an ozone sensor ink.

BACKGROUND OF THE INVENTION

Ozone, by virtue of its high germicidal and other actions, has been utilized for the sterilization and disinfection of foods and instruments or sterilization, disinfection or deodorization of the atmosphere in confined spaces such as the operation theaters of hospitals. On the other hand, ozone is so toxic and deleterious to human health that there is naturally an allowable limit to its concentration. Meanwhile, in photochemical smog forecasts, the atmospheric oxidant level is a significant factor.

For the monitor of ozone concentration, therefore, a variety of methods have been developed for its detection. The principal ozone (oxidant) detection technology available so far takes advantage of the color change according to the following reaction scheme (1).

(O)

$$KI \rightarrow I_2 \qquad (1)$$

As specific detection methods utilizing the above principle, the optical method which comprises introducing an ozone-containing gas into a solution of potassium iodide and measuring the degree of resultant color change, which is proportional to the amount of liberated iodine, by means of a calorimeter and the expedient method utilizing a simple sensor tube are known.

However, the above optical method is not only complicated procedure-wise but time-consuming, failing to provide real-time data. Moreover, the equipment for practicing the method is very expensive. Particularly when a multi-point simultaneous determination is necessary, a plurality of devices must be installed so that the cost adds up to an enormous sum.

The method using a sensor tube is more expedient than the optical detection method. However, the method is still costly and it is necessary to aspirate the oxidant manually or automatically at each determination.

Thus, regardless of which of those known methodologies is utilized, there remains to be developed an expedient and sensitive method for detecting ozone.

SUMMARY OF THE INVENTION

Developed in the above state of the art, the present invention is directed to the following ozone indicator and ozone sensor ink.

1. An ozone indicator comprising (1) at least one color-change layer comprised of an ozone sensor ink and (2) at least one non-color-change layer both formed on a substrate in such a manner that a part or the whole of at least one-color-change layer can be exposed to an ozone-containing atmosphere when the ozone indicator is put to use.

2. An ozone sensor ink comprising an anthraquinone dye having at least one amino group selected from primary and secondary amino groups.

BRIEF DESCRIPTION OF THE DRAWINGS

FIG. 6 is a view showing the design printed in a regular color ink in Example 6.

FIG. 7 is a view showing the design printed in the ozone sensor ink in Example 6.

FIG. 8 is a view showing the design printed in a regular color ink in Example 7.

DETAILED DESCRIPTION OF THE INVENTION

Figure 1:
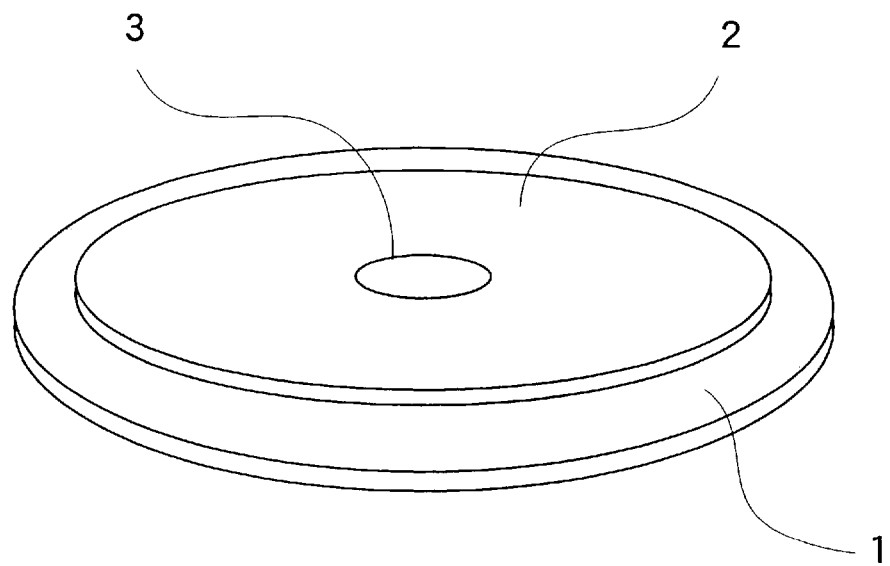
FIG. 1 is a view showing an example of the ozone indicator comprising a color-change layer covered with a transparent resin sheet.

The ozone indicator of the present invention comprises (1) at least one color-change layer comprised of an ozone sensor ink and (2) at least one non-color-change layer both formed on a substrate in such a manner that a part or the whole of at least one color-change layer can be exposed to an ozone-containing atmosphere when the ozone indicator is put to use.

The color-change layer is a layer adapted to undergo change in color in the presence of ozone, and is chiefly comprised of an ozone sensor ink. On the other hand, the non-color-change layer is a layer which does not undergo change in color even in the presence of ozone and is formed using an ink which does not respond color-wise to ozone. In the present invention, the non-color-change layer even includes a substrate itself provided that the substrate does not undergo change in color in the presence of ozone. Therefore, for example, the indicator comprising a color-change layer comprised of an ozone sensor ink formed on a substrate which does not undergo change in color in the presence of ozone is also a species of the ozone indicator of the invention. Moreover, an ozone indicator fabricated by impregnating a substrate not color-wise responding to ozone (paper, nonwoven cloth, etc.) with an ozone sensor ink can also be used as the ozone indicator of the invention. Particularly, for a good discernibility of color change and a greater freedom in design, the non-color-change layer is preferably comprised of an ink which does not undergo change in color upon exposure to ozone.

In fabricating the ozone indicator of the invention, the color-change layer and the non-color-change layer may be formed each as a single layer or a plurality of superimposed layers. Moreover, a color-change layer may be disposed immediately on another color-change layer or a non-color-change layer may be formed on top of another non-color-change layer. In such cases, the plurality of color-change layers may be of the same composition or different compositions. Similarly, the plurality of non-color-change layers may be of the same composition or different compositions.

The color-change layer and the non-color change layer may be formed either on the whole surface or only locally on the surface of a substrate or another layer. For insuring a positive color change of the color-change layer, the color-change and non-color change layers are formed in such a manner that a part or the whole of at least one color-change layer is directly exposed to an ozone-containing atmosphere.

For partial exposure of the color-change layer to an ozone-containing atmosphere, there are several alternative methods which can be used, e.g. the method of forming a non-color-change layer on a color-change layer leaving at least a part of the color-change layer exposed, the method which comprises covering a part of the color-change layer with a cover member made of a known material such as a plastic or glass leaving the remaining part exposed, or the method which comprises forming a color-change layer on a part or the whole of one inner side of a housing provided with at least one opening. The structure obtainable by any of the above and other methods is invariably subsumed in the concept of the ozone indicator of the invention.

There is no particular limitation on the shape or geometry of said member or housing provided that the presence of ozone may be detected. Thus, for example, members of known configurations such as the plate, disk, sheet, etc. and housings of known geometric variations such as the cube, square rod, cylinder, etc. can be mentioned. The material of such a member or housing can be judiciously selected according to the objective of determination and the measuring environment, among other conditions. Particularly preferred are transparent materials such as acrylic resin, celluloid resin, and glass. When a transparent material is used, the zone of color change, color difference, etc. can be easily recognized and assessed from outside. Therefore, provided that this discernibility is satisfied, the material may be colorless and transparent, colored and transparent, or even translucent.

The indicator comprising a color-change layer covered with a known cover member may for example be the indicator illustrated in FIG. 1, that is an indicator comprising a substrate (1) saturated with an ozone sensor ink and a transparent resin sheet (2) as disposed on said substrate. The substrate and the transparent resin sheet are connected to each other with a supporting means (3). The supporting means is not restricted in kind provided that it is capable of supporting the substrate and the transparent resin sheet. Thus, for example, the known cement, adhesive, metal fastener, etc. can be used. In an ozone-containing atmosphere, a color change begins in that part of the color-change layer which is not covered with the transparent resin sheet. Then, ozone diffuses through the clearance between the transparent resin sheet and the substrate or into the substrate gradually to cause the front of color change to advance toward the central part of the substrate. Thus, by using a construction such that the degree of exposure to ozone varies continuously, it is possible to have a zone of color change formed in the color-change layer and accordingly assess the ozone concentration either quantitatively or qualitatively according to the size or configuration of said zone of color change. In this connection, because the member covering the color-change layer is a transparent resin sheet, the zone of color change can be easily recognized from outside.

Figure 2:
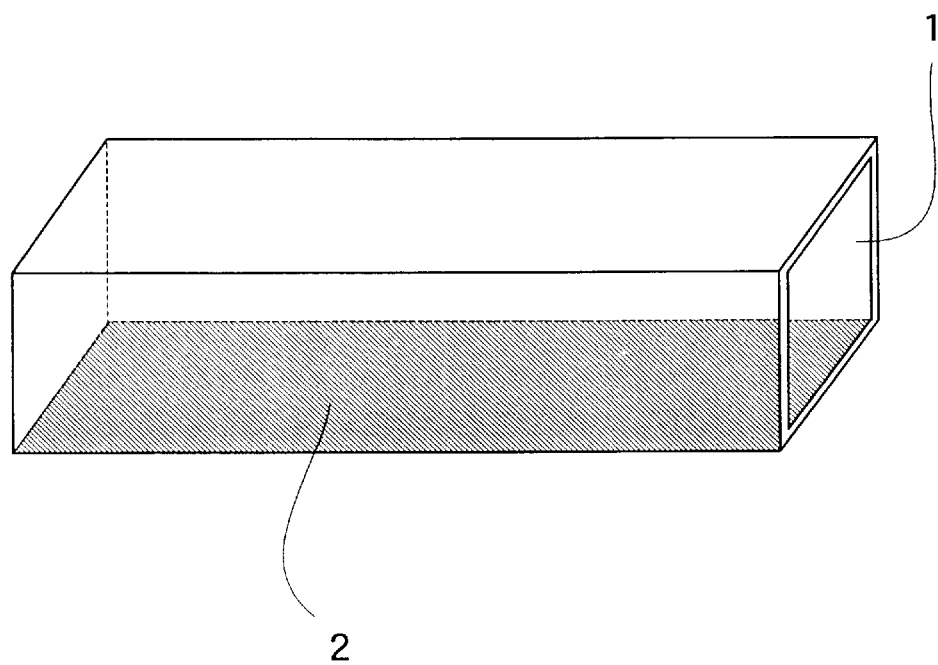
FIG. 2 is a view showing an example of the ozone indicator comprising a color-change layer formed on one inner side of a transparent housing.

The above-mentioned indicator of the housing type may for example be the indicator illustrated in FIG. 2, which comprises a transparent rectangular housing provided with at least one opening (1) and a color-change layer (2) formed by coating an inner side of the housing with an ozone sensor ink. In this indicator, the color change begins to occur in that part of the color-change layer which is adjacent to the opening and progresses inwards gradually. In this case, too, the ozone concentration can be assessed quantitatively or qualitatively according to the size of the color change zone developed in the color-change layer. In addition, because the rectangular housing is made of a transparent material, the zone of color change can be easily recognized from outside. Incidentally, insofar as the color change can be recognized, only a portion of the housing may be transparent. The side of the housing on which the color-change layer is formed is preferably opaque and of a color different from the color that is developed in the color-change layer.

Where necessary, the indicator of the invention may be provided with a means for placing the color-change layer under constant ambient atmospheric conditions. In the present invention, such means includes means for establishing a substantially wind-free condition and means for supplying a wind of constant volume to the color-change layer. The specific means for establishing a substantially wind-free condition may for example comprise installing a wind-shielding device such as a hood so that the color-change layer may be protected from a direct draft of air. The means for sending a wind of constant volume may comprise using a known blower. The type of blower is not particularly restricted provided that it is capable of supplying a constant wind and may for example be a commercial fan or a commercial dryer, or any other known device that is functionally equivalent thereto. In accordance with the invention, insofar as the color-change layer may be placed under constant atmospheric conditions, such a wind shielding device or a blower means may be installed externally of the indicator of the invention. In the sense that the concentration of ozone can be rapidly and accurately measured, it is preferable to employ a means of sending a constant wind to the color-change layer.

The indicator of the invention, when used in association with a means for placing its color-change layer under constant ambient atmospheric conditions, provides for a more accurate and rapid detection of ozone concentration and CT (ozone concentration×exposure time) values. In this sense, the indicator of the invention can be used in various atmospheric environments such as the place where an air conditioner or circulator is available and a windless place which is protected from external disturbances.

Particularly, in accordance with the invention, the ozone concentration and CT can be qualitatively or quantitatively determined from the color difference, the size of the color change zone etc. based on the known data on the relationship of CT with color difference ($\Delta E$), the relationship of CT with the size of the color change zone and the like. For example, by providing graduations corresponding to CT values in the vicinity of the color-change layer of the ozone indicator of the invention, the CT can be determined quantitatively according to the size of the color change zone of the color-change layer. Furthermore, based on the CT value so found, the ozone concentration or the exposure time can be quantitatively or qualitatively determined.

In the present invention, the color-change layer and the non-color-change layer can be formed in such a manner that the color difference between the color-change layer and the non-color-change layer can be recognized only after change of color of the color-change layer or that the color difference between the color-change layer and the non-color-change layer is abolished upon color change of the color-change layer. It is particularly recommendable to form the color-change layer and the non-color-change layer in such a manner that the color difference between the color-change layer and the non-color change layer is discernible only after change of color of the color-change layer.

In connection with the discernibility of a color difference, the color-change layer and the non-color-change layer may be formed in such a manner that at least one of character, pattern and code designs will appear only after change of color of the color-change layer. In the present invention, the character, pattern and code designs include all designs capable of informing a change in color (i.e. the presence of ozone). Such character and other designs can be liberally selected according to the intended application.

In addition, the color of the color-change layer before color change and the color of the non-color-change layer may be dissimilar or such that whereas both layers are of the same color, a discernible color difference (contrast) occurs upon color change of the color-change layer.

In the ozone indicator of the invention, the color-change layer and the non-color change layer may be formed in such a manner that the two layers will not overlap. By so dosing, savings can be realized in the necessary amount of the ink. For example, the color-change layer may be formed on a part of the substrate, with the non-color-change layer being formed on the remaining part or the remaining part of the substrate being left exposed.

As a further embodiment of the present invention, another color-change layer or non-color-change layer may be formed on at least one of said color-change layer and non-color change layer. For example, when another color-change layer of a different design is formed on top of a layer (=color-change/non-color-change layer) formed by disposing a color-change layer and a non-color-change layer in non-overlapping relation, the borderline between the color-change layer and non-color-change layer of the color-change/non-color change layer can be made substantially non-discernible and, hence, a better appearance can be obtained.

The kind of substrate that can be used for the ozone indicator of the invention is not particularly restricted provided that said color-change layer and non-color-change layer can be successfully formed. For example, metals and alloys, wooden materials, paper, ceramics, glass, concrete, plastic, and fibers (nonwoven fabrics, woven fabrics, and other webs or sheets), inclusive of their composites can be mentioned.

The ozone sensor ink for use in the fabrication of said color-change layer is not restricted provided that it undergoes change in color on exposure to an ozone-containing atmosphere but may be a known ink or even a commercial ink. For example, inks prepared by using potassium iodide, a triphenylmethane leuco dye, p-n-butoxyaniline or the like can be used. In the context of the present invention, "color change (or change in color)" is a comprehensive term meaning any and all changes in an initial color (in brightness, hue, etc.), thus including but not limited to fading, discoloration and color development.

In the present invention, it is preferable to use an ink containing an anthraquinone dye having at least one amino group selected from primary and secondary amino groups.

The anthraquinone dye for use in the present invention is not restricted to any specific species provided that it has an anthraquinone nucleus and at least one amino group selected from primary and secondary amino groups. The known anthraquinone disperse dyes can also be used. The dye may have two or more amino groups of the same kind or different kinds.

The anthraquinone dye as such includes but is not limited to 1,4-diaminoanthraquinone (C. I. Disperse Violet 1), 1-amino-4-hydroxy-2-methoxyanthraquinone (C. I. Disperse Red 4), 1-amino-4-methylaminoanthraquinone (C. I. Disperse Violet 4), 1,4-diamino-2-methoxyanthraquinone (C. I. Disperse Red 11), 1-amino-2-methylanthraquinone (C. I. Disperse Orange 11), 1-amino-4-hydroxyanthraquinone (C. I. Disperse Red 15), 1,4,5,8-tetraaminoanthraquinone (C. I. Disperse Blue 1), and 1,4-diamino-5-nitroanthraquinone (C. I. Disperse Violet 8) etc.[proprietary dye numbers in parentheses]. In addition, dyes known as C. I. Solvent Blue 14, C. I. Solvent Blue 63, C. I. Solvent Violet 13, C. I. Solvent Violet 14, C. I. Solvent Red 52, C. I. Solvent Red 114, C. I. Vat Blue 21, C. I. Vat Blue 30, C. I. Vat Violet 15, C. I. Vat Violet 17, C. I. Vat Red 19, C. I. Vat Red 28, C. I. Acid Blue 23, C. I. Acid Blue 80, C. I. Acid Violet 43, C. I. Acid Violet 48, C. I. Acid Red 81, C. I. Acid Red 83, C. I. Reactive Blue 4, C. I. Reactive Blue 19, C. I. Disperse Blue 7, etc. can also be employed. Those anthraquinone dyes can be used each independently or in combination. Preferred among those anthraquinone dyes are C. I. Digperse Blue 7 and C. I. Disperse Violet 1. Furthermore, in the practice of the invention, the ozone detection sensitivity can be controlled by modifying the description (e.g. molecular structure) of those anthraquinone dyes.

In the practice of the invention, the ink containing such an anthraquinone dye as above is more preferably supplemented with a cationic surfactant of the quaternary ammonium salt type.

The cationic surfactant of the quaternary ammonium salt type (hereinafter sometimes referred to briefly as "cationic surfactant") is not particularly restricted. Alkylammonium salts are usually selected and commercial products can be used for the purpose. Moreover, such surfactants can be used each independently or as a mixture of two or more species. In the present invention, an improved ozone detection sensitivity can be obtained by using such a cationic surfactant in combination with said anthraquinone dye.

Preferred among such cationic surfactants are alkyltrimethylammonium salts and dialkyldimethylammonium salts. Specifically, coco-alkyltrimethylammonium chloride, tallow-alkyltrimethylammonium chloride, behenyltrimethylammonium chloride, hexadecyltrimethylammonium chloride, lauryltrimethylammonium chloride, octadecyltrimethylammonium chloride, dioctyldimethylammonium chloride, distearyldimethylammonium chloride, alkylbenzyldimethylammonium chloride, etc. can be mentioned. Particularly preferred is lauryltrimethylammonium chloride.

The ink for the present invention may be supplemented with various formulating agents such as those incorporated in known inks, for example a resinous binder, an extender, a solvent, and so forth.

The resinous binder can be judiciously selected according to the type of substrate, for instance, and the known component resins included in writing or printing ink compositions can be used as such. To mention some specific examples, maleic acid resin, amide resin, ketone resin, alkylphenol resin, rosin-modified resin, poly(vinyl butyral), poly(vinylpyrrolidone), and cellulosic resin can be used.

The extender is not particularly restricted but includes bentonite, active terra alba, aluminum oxide, silica gel, and so forth. Aside from the above-mentioned extenders, various substances known as extender pigments can also be used. Particularly preferred, among them, are porous extenders. Silica gel, in particular, is still more preferred. By adding such an extender, the detection sensitivity, in the main, can be controlled.

The solvent species which can be used in the present invention includes all those solvents which are generally used in printing or writing ink compositions. For example, solvents in the alcohol series, ester series, ether series, ketone series, and hydrocarbon series can be selectively used according to the solubility of the dye and resinous binder, among other parameters.

The amounts of those formulating agents can be judiciously selected according to their kinds and the intended uses. For example, when an ink containing said anthraquinone dye is used as the ozone sensor ink, the usual concentration of the anthraquinone dye in the ink may range from 0.05 to 5 weight % (preferably 0.1–1 weight %) and this basal formulation may be adjusted with 50 weight % or less (preferably 5–35 weight %) of said resinous binder and 1–30 weight % (preferably 2–20 weight %) of said extender.

When a cationic surfactant is added, the usual formulation may be 0.05–10 weight % (preferably 0.1–1 weight %) of the anthraquinone dye, 0.2–30 weight % (preferably 0.5–10 weight %) of the cationic surfactant and this basal formulation may be adjusted with 50 weight % or less (preferably 5–35 weight %) of said binder and 1–30 weight % (preferably 2–20 weight %) of said extender.

Those components can be added at one time or sequentially and evenly blended using a known mixing machine such as a homogenizer, a dessolver, or the like. An exemplary procedure comprises adding the anthraquinone dye, cationic surfactant, resinous binder, and extender serially to the solvent and mixing them together under agitation.

On the other hand, as the ink for said non-color-change layer, any ink can be used provided that it does not undergo change in color upon exposure to ozone. As the ink as such, commercial regular inks can be used. For example, water-based inks, oil-based inks, solvent-less inks, etc. can be mentioned. In the case of printing, the known relief printing ink, gravure printing ink, screen printing ink, offset printing ink, etc. can be selectively used according to the printing method adopted. Those inks can be used each independently or as blended for color mixing. It should be understood that the ink for the non-color-change layer may contain those components which are usually included in known inks (e.g. resinous binder, extender, solvent, etc.).

The formation of the color-change layer and non-color-change layer in the present invention can be carried out by the known printing techniques such as silk screen printing, gravure printing, offset printing, relief printing, flexo printing, etc. using inks suited for the respective techniques. The order of printing for the color-change layer and the non-color-change layer is not critical and can be chosen according to the design to be printed. Those layers can be respectively formed by dipping the substrate in the respective inks. This technique is particularly suited for substrates which are permeable to the ink, such as paper and nonwoven fabrics.

According to the ozone indicator of the ininvention, comprising a specific combination of color-change and non-color-change layers, the color change can be detected accurately, thereby the presence of ozone can be recognizd easily. Furthermore, when the whole architecture of the indicator is a sheet or a board, it does not take space and, when a judicious substrate is chosen, is flexible, so that it can be installed in any desired position or location.

Furthermore, by adopting a judicious combination of said color-change and non-color-change layers, the pattern, character and code designs pertinent to intended applications can be represented so as to impart an aesthetic/functional value and insure a versatility of use.

Moreover, by adopting an architecture such that the progress or degree of exposure to ozone is expressed continually as typically illustrated in FIGS. 1 and 2, the ozone concentration and CT can be qualitatively or quantitatively assessed according to the size of color change zone and/or the color difference.

When the ozone sensor ink of the invention is used in the formation of the color-change layer, it reacts effectively with ozone to undergo change in color even when it is in a substantially dry condition, insuring still more improved detection accuracy (selectivity), sensitivity, and stability and even an improved discernibility of the presence of ozone by the naked eye. In addition, by varying the kinds and formulating amounts of said anthraquinone dye, extender, and other components, the detection sensitivity and the speed of color change can be freely controlled, thus enabling a still more positive detection of ozone concentration.

The ozone sensor ink of the invention undergoes fading or discoloration upon contact with ozone even when it is a substantially dry condition, to the extent permitting a visual detection of the presence of ozone, and is very satisfactory in the accuracy (selectivity), sensitivity, and stability of detection. Particularly when a cationic surfactant of the quaternary ammonium salt type is included in the formulation, a still more satisfactory color-change response can be obtained to permit a positive detection of still lower concentrations of ozone. Depending on conditions, even ozone in a low concentration of 0.03 ppm can be successfully detected.

Furthermore, by varying the kinds and formulating amounts of the anthraquinone dye and other components, the detection sensitivity and color change speed of the ink of the invention can be freely controlled.

In addition, by formulating a resinous binder, the ink of the invention can be used as a printing ink, writing ink, or a stamp ink. Moreover, the ink can be used in the form of a paper, film or other matrix coated or saturated with it. Thus, by forming several ink layers on a substrate using several kinds of inks of the invention which fade or discolor at discrete ozone levels, a convenient ozone indicator can be provided.

EXAMPLES

Example 1

Using a mixer, 0.20 part by weight of anthraquinone disperse dye [Miketon Fast Red Violet R, Mitsui-BASF Co.], 7.35 parts by weight of ethylcellulose resin (Ethocel 10, Dow Chemical Co.) as resinous binder, 9.80 parts by weight of silica gel [Aerosil R-972, Japan Aerosil Co.], 1.96 parts by weight of coco-alkyltri-methylammonium chloride [CA-2150, Nikkol Co.] as cationic surfactant, and 80.69 parts by weight of ethylcellosolve [Seahosol MG, Nippon Shokubai Co.] as solvent were mixed uniformly to provide an ozone sensor ink.

Example 2

Except that 1.96 parts by weight of lauryltrimethylammonium chloride [Coatamine 24P, Kao Co.] was used as cationic surfactant, the procedure of Example 1 was otherwise repeated to provide an ozone sensor ink.

Example 3

Using a mixer, 0.24 part by weight of anthraquinone disperse dye [Miketon Fast Turquoise Blue G, Mitsui-BASF Co.], 9.15 parts by weight of ethylcellulose resin [Ethocel 10, Dow Chemical Co.] as resinous binder, 12.20 parts by weight of silica gel [Aerosil R-972, Japan Aerosil Co.], 2.44 parts by weight of hexadecyltrimethylammonium chloride [Cation PB-40, Nippon Oil and Fat Co.] as cationic surfactant, and 75.97 parts by weight of ethylcellulose [Seahosol MG, Nippon Shokubai Co.] as solvent were mixed uniformly to provide an ozone sensor ink.

Test Example 1

The color change performance was evaluated using the inks prepared in Examples 1–3 and Comparative Examples 1–2. Using each ink, Kent paper was printed by silk screen (150 mesh) printing. When the print was exposed to an atmosphere containing 0.3 ppm of ozone for about 15 minutes, the time course of fading or discoloration of the printed color was apparent to the unaided eye. The color difference ($\Delta E$) between the color after exposure to ozone and the initial color before exposure (before color change) was determined. The results are presented in Table 1.

TABLE 1

|  | Color difference ($\Delta E$) |
| --- | --- |
| Example 1 | 43.2 |
| Example 2 | 48.8 |
| Example 3 | 45.6 |

It is clear from Table 1 that the color difference is large and the color residue is small in Examples 1–3, indicating that the ozone sensor ink of the invention is sensitive enough to detect ozone even when the atmospheric concentration of ozone is as low as 0.3 ppm.

Example 4

Using the ozone sensor ink prepared in Example 1, an ozone indicator was fabricated. On the other hand, a regular color ink for the non-color-change layer was prepared. Thus, 60.6 parts by weight of white ink [Conc 061-a], 6.1 parts by weight of purple ink [082-A], and 33.3 parts by weight of medium ink [Medium] [all in the Serikol JM Series (Matte Type), Teikoku Ink Co.] were mixed to prepare the regular color ink (light purple color).

Figure 3:
FIG. 3 is a view showing the design printed in the ozone sensor ink in Examples 4 and 5.
Figure 4:
FIG. 4 is a view showing the design printed in a regular color ink in Examples 4 and 5.

Using the ozone sensor ink, the character design (dropout characters) illustrated in FIG. 3 was printed on Kent paper by silk screen (150 mesh) printing to provide a color-change layer. Then, avoiding overlap with the color-change layer, the character design illustrated in FIG. 4 was printed using the regular color ink by silk screen (300 mesh) printing to provide a non-color-change layer. In this manner, an indicator which was light purple all over was obtained. In the practice of the invention, whichever of the ozone sensor ink and the regular color ink can be used for the design illustrated in FIG. 3 or the design illustrated in FIG. 4. Moreover, it does not matter which of the designs is printed first.

The indicator obtained in the above manner was allowed to stand in an ozone-containing atmosphere (ozone concentration about 0.3 ppm) for 15 minutes. As a result, the color-change layer consisting in said dropout characters was selectively discolored so that the characters of the non-color-change layer became discernible as light purple characters.

Example 5

An ozone sensor ink was first prepared. Thus, 0.24 part by weight of anthraquinone disperse dye [Miketon Fast Red Violet R, Mitsui-BASF Co.], 9.15 parts by weight of ethylcellulose resin [Ethocel 10, Dow Chemical Co.] as resinous binder, 12.20 parts by weight of silica gel as extender pigment, and 78.41 parts by weight of ethylcellosolve [Seahosol MG, Nippon Shokubai Co.] were mixed uniformly to provide an ozone sensor ink (light purple color).

On the other hand, a regular color ink for the non-color-change layer was prepared. Thus, 60.6 parts by weight of white ink [Conc 061-a], 6.1 parts by weight of purple ink [082-A], and 33.3 parts by weight of medium ink [Medium] [all in the Serikol JM Series (Matte Type), Teikoku Ink Co.] were mixed to prepare the regular color ink (light purple color).

Using the ozone sensor ink, the character design (dropout characters) illustrated in FIG. 3 was printed on Kent paper by silk screen (150 mesh) printing to provide a color-change layer. Then, avoiding overlap with the color-change layer, the character design illustrated in FIG. 4 was printed using the regular color ink by silk screen (300 mesh) printing to provide a non-color-change layer. In this manner, an indicator which was light purple all over was obtained. In the practice of the invention, whichever of the ozone sensor ink and the regular color ink can be used for the design illustrated in FIG. 3 or the design illustrated in FIG. 4. Moreover, it does not matter which of the designs is printed first.

The indicator obtained in the above manner was allowed to stand in an ozone-containing atmosphere (ozone concentration: about 0.3 ppm) for 15 minutes. As a result, the color-change layer consisting in said dropout characters was selectively discolored so that the characters of the non-color-change layer became discernible as light purple characters.

Example 6

An ozone indicator was fabricated using the same ozone sensor ink and regular color ink as used in Example 5.

Figure 5:
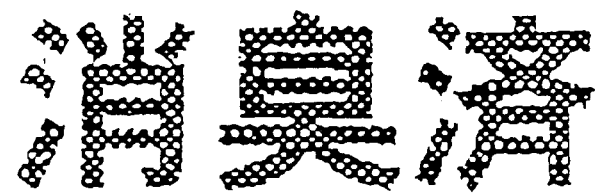
FIG. 5 is a view showing the design printed in the ozone sensor ink in Example 6.

First, the character design illustrated in FIG. 5 was printed on Kent paper using the ozone sensor ink by silk screen (150 mesh) printing to provide a color-change layer. Then, avoiding overlap with the color-change layer, the character design (dropout characters) illustrated in FIG. 6 was printed using the regular color ink by silk screen (300 mesh) printing to provide a non-color-change layer. Thereafter, over the surface of the non-color-change layer, the character design (fine English language text) illustrated in FIG. 7 was printed using the ozone sensor ink by silk screen (300 mesh) printing to provide a color-change layer. After formation of this color-change layer, the borderline which was initially slightly conspicuous became substantially undiscernible.

When the indicator thus obtained was left standing in an ozone-containing atmosphere (ozone concentration: about 0.3 ppm) for 15 minutes, the color-change layer corresponding to the English language text discolored first, then the color-change layer corresponding to the dropout characters (the exposed zone of the color-change layer) faded away, and finally the white letters appeared due to contrast with the non-color-change layer.

Example 7

As the regular color ink for the non-color-change layer, 38.8 parts by weight of white ink [Conc 061-a], 2.6 parts by weight of purple ink [082-A], 0.9 part by weight of ultramarine blue ink [037-b], and 57.7 parts by weight of medium ink [Medium] [all in the Serikol JM Series (Matte Type), Teikoku Ink Co.] were blended for color mixing. On the other hand, as the ozone sensor ink, the same ink as used in Example 5 was used.

First, the ozone sensor ink was printed solid on Kent paper by silk screen (300 mesh) printing to provide a color-change layer. Then, over the entire surface of the color-change layer, the character design (dropout characters) illustrated in FIG. 8 was printed using the regular color ink by silk screen (300 mesh) printing to provide a non-color-change layer.

The resulting indicator was allowed to stand in an ozone-containing atmosphere (ozone concentration: about 0.3 ppm) for 15 minutes. As a result, the color-change layer corresponding to the dropout characters (the exposed zone of the color-change layer) faded away and finally white characters appeared due to contrast with the non-color-change layer.

Example 8

0.25 Part by weight of anthraquinone disperse dye [Miketon Fast Red Violet R, Mitsui-BASF Co.], 6.25 parts by weight of ethylcellulose resin [Ethocel 10, Dow Chemical Co.] as resinous binder, 3.13 weight of maleic acid resin [Malkyd 33, Arakawa Chemical Co.], 6.25 parts by weight of silica gel as extender, and 84.12 parts by weight of ethylcellosolve as solvent were mixed uniformly to provide an ozone sensor ink.

Example 9

0.25 Part by weight of anthraquinone disperse dye [Miketon Fast Turquoise Blue G, Mitsui-BASF Co.], 9.38 parts by weight of ethylcellulose resin [Ethocel 10, Dow Chemical Co.] as resinous binder, 12.50 parts by weight of silica gel as extender, and 77.87 parts by weight of ethylcellosolve as solvent were mixed uniformly to provide an ozone sensor ink.

Example 10

0.30 Part by weight of anthraquinone disperse dye [Miketon Fast Blue Extra, Mitsui-BASF Co.], 6.25 parts by weight of ethylcellulose resin [Ethocel 10, Dow Chemical Co.] as resinous binder, 10.00 parts by weight of silica gel as extender, and 83.45 parts by weight of ethylcellosolve as solvent were mixed uniformly to provide an ozone sensor ink.

Test Example 2

The performance of the ozone sensor ink containing the anthraquinone dye in accordance with the invention was evaluated.

Using the ozone sensor inks prepared in Examples 8–10, respectively, and the silk screen printing technique, Kent paper was coated to prepare samples. Those samples were exposed to ozone under the conditions shown in Table 1 and the color change performance of each sample was grossly evaluated. The evaluation criteria were "o" for the case in which a color change was easily recognized and "x" for the case in which the color change could not be easily recognized. As a color retentivity parameter, the difference between the color immediately after color change and the color after 3 days of subsequent standing at 50° C. was determined. The results are also shown in Table 2. For comparison's sake, the conventional indicator (potassium iodide-starch paper) was also tested in the same manner. The results are shown in the column of Comparative Example 1.

TABLE 2

|  | Example 8 | Example 9 | Example 10 | Comparative Example 1 |
| --- | --- | --- | --- | --- |
| Color change performance, 5 ppm × 15 min. | o | o | o | o |
| Color change performance, 1 ppm × 15 min. | o | o | o | X |
| Color change performance, 0.3 ppm × 15 min. | o | o | o | X |
| Color retention after color change | o | o | o | X |

It is clear from Table 2 that the conventional indicator detects ozone under the conditions of 5 ppm×15 min. but fails to detect lower concentrations of ozone and that, in contract, the ozone sensor ink of the invention responds sensitively to ozone even when the concentration of ozone is as low as 1 ppm or 0.3 ppm.

What is claimed is:

1. An ink composition comprising (i) an anthraquinone dye having at least one amino group selected from the group consisting of primary and secondary amino groups in an amount effective to visually change its color when exposed to ozone in an ozone-containing atmosphere, (ii) a quaternary ammonium salt cationic surfactant in an amount effective to enhance the visual change in color, and (iii) an extender and (iv) a binder.

2. The ink composition according to claim 1, wherein the anthraquinone dye is contained in an amount of 0.05%–10% by weight, the quaternary ammonium salt cationic surfactant is contained in an amount of 0.2%–30% by weight, the extender is contained in an amount of 1%–30% by weight, and the binder is contained in an amount of no more than 50% by weight.

3. The ink composition according to claim 1, wherein the cationic surfactant is an alkylmethylammonium salt.

4. The ink composition according to claim 1, wherein the extender is a silica gel.

5. The ink composition according to claim 1, wherein the binder is a resinous binder.

6. The ink composition according to claim 5, wherein the resinous binder is contained in an amount of 5%–35% by weight.

7. An ink composition comprising (i) 0.05%–10% by weight of an anthraquinone dye having at least one amino group selected from the group consisting of primary and secondary amino groups, (ii) 0.2%–30% by weight of a quaternary ammonium salt cationic surfactant, (iii) 1%–30% by weight of an extender, and (iv) no more than 50% by weight of a binder.

8. An ink composition comprising (i) an anthraquinone dye having at least one amino group selected from primary and secondary amino groups, and (ii) a quaternary ammonium salt type cationic surfactant, wherein the cationic surfactant is an alkylmethylammonium salt.

9. An ink composition comprising (i) an anthraquinone dye having at least one amino group selected from primary and secondary amino groups, (ii) a quaternary ammonium salt type cationic surfactant, and (iii) an extender.

10. The ink composition according to claim 9, wherein the extender is a silica gel.

11. The ink composition according to claim 9, further comprising a resinous binder.

12. The ink composition according to claim 11, wherein the resinous binder is contained in an amount of 5%–35% by weight.

* * * * *